(12) United States Patent
Grey

(10) Patent No.: US 7,767,835 B2
(45) Date of Patent: Aug. 3, 2010

(54) DIRECT EPOXIDATION PROCESS USING IMPROVED CATALYST

(75) Inventor: Roger A. Grey, West Chester, PA (US)

(73) Assignee: Lyondell Chemical Technology, L.P., Greenville, DE (US)

(*) Notice: Subject to any disclaimer, the term of this patent is extended or adjusted under 35 U.S.C. 154(b) by 0 days.

(21) Appl. No.: 12/317,012

(22) Filed: Dec. 18, 2008

(65) Prior Publication Data

US 2010/0160654 A1    Jun. 24, 2010

(51) Int. Cl.
*C07D 301/06* (2006.01)

(52) U.S. Cl. .................. 549/533; 502/66; 502/242; 502/311; 502/326; 502/349

(58) Field of Classification Search ............... 549/533; 502/66, 242, 311, 326, 349
See application file for complete search history.

(56) References Cited

U.S. PATENT DOCUMENTS

| | | | |
|---|---|---|---|
| 3,351,635 A | 11/1967 | Kollar | |
| 3,607,728 A | 9/1971 | Wilhelm | |
| 4,083,806 A | 4/1978 | Wilhelm | |
| 4,130,597 A | 12/1978 | Wilhelm | |
| 4,367,342 A | 1/1983 | Wulff et al. | |
| 4,410,501 A | 10/1983 | Taramasso et al. | |
| 4,666,692 A | 5/1987 | Taranasso et al. | |
| 4,833,260 A | 5/1989 | Neri et al. | |
| 4,859,785 A | 8/1989 | Bellussi et al. | |
| 4,937,216 A | 6/1990 | Clerici et al. | |
| 4,939,110 A | 7/1990 | Sachtler et al. | |
| 5,892,102 A | 4/1999 | Mikami et al. | |
| 6,005,123 A | 12/1999 | Dessau et al. | |
| 6,008,388 A | 12/1999 | Dessau et al. | |
| 6,399,794 B1 | 6/2002 | Hancu | |
| 6,498,259 B1 | 12/2002 | Grey et al. | |
| 7,026,492 B1 | 4/2006 | Kaminsky | |
| 7,387,981 B1 | 6/2008 | Kaminsky et al. | |
| 2003/0040635 A1 | 2/2003 | Jansen et al. | |
| 2003/0162656 A1 | 8/2003 | Wu et al. | |
| 2007/0203372 A1* | 8/2007 | Ramakers | 568/867 |
| 2008/0021230 A1 | 1/2008 | Qin et al. | |

FOREIGN PATENT DOCUMENTS

| | | |
|---|---|---|
| EP | 0972759 | 1/2000 |
| GB | 1374300 | 12/1971 |
| JP | 4-352771 | 5/1991 |
| WO | WO 98/00413 | 1/1998 |
| WO | WO 2008/123912 | 10/2008 |
| WO | WO 2009/054876 | 4/2009 |

* cited by examiner

*Primary Examiner*—Janet L Andres
*Assistant Examiner*—David E Gallis
(74) *Attorney, Agent, or Firm*—Kevin M. Carroll

(57) ABSTRACT

A supported catalyst and a catalyst mixture, useful for the direct epoxidation of olefins, are disclosed. The supported catalyst comprises a noble metal, lead, and a carrier that has been treated by contacting with nitric acid. The catalyst mixture comprises a titanium or vanadium zeolite and the supported catalyst. The invention also includes a process for producing an epoxide comprising reacting an olefin, hydrogen and oxygen in the presence of the catalyst mixture. The process results in significantly reduced alkane byproduct formed by the hydrogenation of olefin.

13 Claims, No Drawings

US 7,767,835 B2

DIRECT EPOXIDATION PROCESS USING IMPROVED CATALYST

FIELD OF THE INVENTION

This invention relates to a supported catalyst, a catalyst mixture, and its use in the production of epoxides from hydrogen, oxygen, and olefins.

BACKGROUND OF THE INVENTION

Many different methods for the preparation of epoxides have been developed. Generally, epoxides are formed by the reaction of an olefin with an oxidizing agent in the presence of a catalyst. Ethylene oxide is commercially produced by the reaction of ethylene with oxygen over a silver catalyst. Propylene oxide is commercially produced by reacting propylene with an organic hydroperoxide oxidizing agent, such as ethylbenzene hydroperoxide or tert-butyl hydroperoxide. This process is performed in the presence of a solubilized molybdenum catalyst, see U.S. Pat. No. 3,351,635, or a heterogeneous titania on silica catalyst, see U.S. Pat. No. 4,367,342.

Besides oxygen and alkyl hydroperoxides, hydrogen peroxide is also a useful oxidizing agent for epoxide formation. U.S. Pat. Nos. 4,833,260, 4,859,785, and 4,937,216, for example, disclose olefin epoxidation with hydrogen peroxide in the presence of a titanium silicate catalyst.

Much current research is conducted in the direct epoxidation of olefins with oxygen and hydrogen. In this process, it is believed that oxygen and hydrogen react in situ to form an oxidizing agent. Many different catalysts have been proposed for use in the direct epoxidation process. Typically, the catalyst comprises a noble metal and a titanosilicate. For example, JP 4-352771 discloses the formation of propylene oxide from propylene, oxygen, and hydrogen using a catalyst containing a Group VIII metal such as palladium on a crystalline titanosilicate. The Group VIII metal is believed to promote the reaction of oxygen and hydrogen to form a hydrogen peroxide in situ oxidizing agent. U.S. Pat. No. 6,498,259 describes a catalyst mixture of a titanium zeolite and a supported palladium complex, where palladium is supported on carbon, silica, silica-alumina, titania, zirconia, and niobia. Other direct epoxidation catalyst examples include gold supported on titanosilicates, see for example PCT Intl. Appl. WO 98/00413.

One disadvantage of the described direct epoxidation catalysts is that they are prone to produce non-selective byproducts such as glycols or glycol ethers formed by the ring-opening of the epoxide product or alkane byproduct formed by the hydrogenation of olefin. U.S. Pat. No. 6,008,388 teaches that the selectivity for the direct olefin epoxidation process is enhanced by the addition of a nitrogen compound such as ammonium hydroxide to the reaction mixture. U.S. Pat. No. 6,399,794 teaches the use of ammonium bicarbonate modifiers to decrease the production of ring-opened byproducts.

U.S. Pat. No. 6,005,123 teaches the use of phosphorus, sulfur, selenium or arsenic modifiers such as triphenylphosphine or benzothiophene to decrease the production of propane. U.S. Pat. No. 7,026,492 discloses that the presence of carbon monoxide, methylacetylene, and/or propadiene modifier gives significantly reduced alkane byproduct. U.S. Appl. Pub. No. 2008/0021230 discloses that the use of a lead-modified palladium-containing titanium or vanadium zeolite reduces alkane byproduct formation. In addition, co-pending U.S. patent application Ser. No. 11/977,360 teaches that the use of a catalyst comprising titanium or vanadium zeolite, a noble metal, lead, and bismuth also reduces alkane byproduct formation.

As with any chemical process, it is desirable to attain still further improvements in the epoxidation methods and catalysts. We have discovered a new catalyst and its use in olefin epoxidation.

SUMMARY OF THE INVENTION

The invention is a supported catalyst comprising a noble metal, lead, and a carrier that has been treated by contacting with nitric acid. The invention also comprises a catalyst mixture comprising a titanium or vanadium zeolite and the supported catalyst. The catalyst mixture is useful in olefin epoxidation. Thus, the invention also includes an olefin epoxidation process that comprises reacting olefin, oxygen, and hydrogen in the presence of the catalyst mixture. This process surprisingly gives significantly reduced alkane byproduct formed by the hydrogenation of olefin.

DETAILED DESCRIPTION OF THE INVENTION

The supported catalyst of the invention comprises a noble metal, lead and a carrier. The carrier is preferably an inorganic porous material, in particular inorganic oxides and clays. The carrier is most preferably an inorganic oxide. Preferred inorganic oxides include oxides of Group 2, 3, 4, 5, or 14 elements. Particularly preferred inorganic oxide carriers include silica, titania, zirconia, niobium oxides, tantalum oxides, amorphous titania-silica, amorphous zirconia-silica, amorphous niobia-silica, and the like. The carrier may be a zeolite, but is not a titanium or vanadium zeolite. Particularly preferred inorganic oxides include silica, titania, zirconia, and niobia. Titania is most preferred.

Preferably, the carrier has a surface area in the range of about 1 to about 1000 $m^2/g$, most preferably from about 10 to about 500 $m^2/g$. Preferably, the pore volume of the carrier is in the range of about 0.1 to about 4.0 mL/g, more preferably from about 0.5 to about 3.5 mL/g, and most preferably from about 0.8 to about 3.0 mL/g. Preferably, the average particle size of the carrier is in the range of about 0.1 μm to about 1.4 cm, more preferably from about 1 μm to about 0.7 cm, and most preferably from about 10 μm to about 0.2 cm. The preferred particle size is dependent upon the type of reactor that is used, for example, larger particle sizes are preferred for a fixed bed reaction. The average pore diameter is typically in the range of about 10 to about 1000 Å, preferably about 20 to about 500 Å, and most preferably about 50 to about 350 Å.

The supported catalyst also contains a noble metal and lead. While any of the noble metals can be utilized (i.e., gold, silver, platinum, palladium, iridium, ruthenium, osmium), either alone or in combination, palladium, platinum, gold, a palladium/platinum, or a palladium/gold combination are particularly desirable. Palladium is most preferred.

Typically, the amount of noble metal present in the supported catalyst will be in the range of from 0.01 to 20 weight percent, preferably 0.1 to 10 weight percent. The manner in which the noble metal is incorporated into the supported catalyst is not considered to be particularly critical. For example, a noble metal compound (e.g., palladium dinitrate) may be supported on the carrier by impregnation, adsorption, ion-exchange, precipitation, or the like.

There are no particular restrictions regarding the choice of noble metal compound or complex used as the source of noble metal in the supported catalyst. For example, suitable compounds include the nitrates, sulfates, halides (e.g., chlorides, bromides), carboxylates (e.g. acetate), oxides, and amine complexes of the noble metal.

Similarly, the oxidation state of the noble metal is not considered critical. In the case of palladium for instance, the palladium may be in an oxidation state anywhere from 0 to +4 or any combination of such oxidation states. To achieve the desired oxidation state or combination of oxidation states, the noble metal compound after being introduced into the supported catalyst may be fully or partially pre-reduced. Satisfactory catalytic performance can, however, be attained without any pre-reduction.

The supported catalyst of the invention also contains lead. The typical amount of lead present in the supported catalyst will be in the range of from about 0.01 to 10 weight percent, preferably 0.01 to 2 weight percent. Suitable lead compounds used as the lead source in the supported catalyst include lead nitrates, carboxylates (e.g., acetate), halides (e.g., chlorides, bromides, iodides), cyanides, and sulfides. Lead nitrates and carboxylates are particularly preferred. Lead nitrates are most preferred. The lead may be added to the carrier before, during, or after noble metal addition. Any suitable method can be used for the incorporation of lead into the supported catalyst. As with noble metal addition, the lead may be supported on the carrier by impregnation (e.g., by incipient wetness, etc.), adsorption, ion-exchange, deposition-precipitation, or other incorporation methods.

The carrier is treated by contacting with nitric acid. The nitric acid is preferably an aqueous solution containing 1 to 70 weight percent nitric acid. The contacting can be performed in a batch or continuous manner, preferably in a batch manner. The temperature of the contacting is not critical, but temperatures of from 15 to 60° C. are preferred. The amount of time required for contacting is not critical, but will typically be from about 0.1 to 24 hours.

The carrier may be contacted with nitric acid in a variety of ways, including, but not limited to, the following means. The nitric acid treatment may be performed: (1) prior to the addition of the noble metal and lead compounds; (2) simultaneously with the addition of the noble metal compound, either prior to or following addition of lead compound; (3) simultaneously with the addition of lead compound, either prior to or following addition of the noble metal compound; (4) simultaneously with the addition of both the noble metal and lead compounds; and (5) following the addition of the noble metal and lead compounds.

After nitric acid treatment, and noble metal and lead incorporation, the supported catalyst is recovered. Suitable catalyst recovery methods include filtration and washing, rotary evaporation and the like. The supported catalyst is preferably dried at a temperature greater than about 50° C. prior to use in epoxidation. The drying temperature is preferably from about 50° C. to about 700° C., and more preferably from about 250° C. to about 450° C. The supported catalyst may be optionally thermally treated in a gas such as nitrogen, helium, vacuum, hydrogen, oxygen, air, or the like. The thermal treatment temperature is typically from about 50° C. to about 700° C. It is preferred to thermally treat the supported catalyst in the presence of an oxygen-containing gas at a temperature from about 400° C. to about 650° C., and optionally reduce the supported catalyst in the presence of a hydrogen-containing gas at a temperature from about 50° C. to about 300° C.

The supported catalyst may additionally comprise a binder or the like and may be molded, spray dried, shaped or extruded into any desired form prior to use in epoxidation.

The catalyst mixture of the invention comprises the supported catalyst and a titanium or vanadium zeolite. Titanium or vanadium zeolites comprise the class of zeolitic substances wherein titanium or vanadium atoms are substituted for a portion of the silicon atoms in the lattice framework of a molecular sieve. Such substances, and their production, are well known in the art. See for example, U.S. Pat. Nos. 4,410,501 and 4,666,692.

Suitable titanium or vanadium zeolites are those crystalline materials having a porous molecular sieve structure with titanium or vanadium atoms substituted in the framework. The choice of titanium or vanadium zeolite employed will depend upon a number of factors, including the size and shape of the olefin to be epoxidized.

Particularly preferred titanium or vanadium zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), "TS-3" (as described in Belgian Pat. No. 1,001,038), and Ti-MWW (having a topology analogous to that of the MWW aluminosilicate zeolites). Titanium-containing molecular sieves having framework structures isomorphous to zeolite beta, mordenite, ZSM-48, ZSM-12, SBA-15, TUD, HMS, and MCM-41 are also suitable for use. TS-1 and Ti-MWW are particularly preferred. The titanium zeolites preferably contain no elements other than titanium, silicon, and oxygen in the lattice framework, although minor amounts of boron, iron, aluminum, sodium, potassium, copper and the like may be present.

Preferred titanium zeolites will generally have a composition corresponding to the following empirical formula $xTiO_2$ $(1-x)SiO_2$ where x is between 0.0001 and 0.5000. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable.

The epoxidation process of the invention comprises contacting an olefin, oxygen, and hydrogen in the presence of the catalyst mixture comprising a titanium or vanadium zeolite and a supported catalyst comprising a noble metal, lead and a carrier that has been treated by contacting with nitric acid. Suitable olefins include any olefin having at least one carbon-carbon double bond, and generally from 2 to 60 carbon atoms. Preferably the olefin is an acyclic alkene of from 2 to 30 carbon atoms; the process of the invention is particularly suitable for epoxidizing $C_2$-$C_6$ olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro groups, or the like. The process of the invention is especially useful for converting propylene to propylene oxide.

Oxygen and hydrogen are also required for the epoxidation process. Although any sources of oxygen and hydrogen are suitable, molecular oxygen and molecular hydrogen are preferred.

Epoxidation according to the invention is carried out at a temperature effective to achieve the desired olefin epoxidation, preferably at temperatures in the range of 0-250° C., more preferably, 20-100° C. The molar ratio of hydrogen to oxygen is preferably in the range of $H_2:O_2=1:10$ to 5:1 and is especially favorable at 1:5 to 2:1. The molar ratio of oxygen to olefin is preferably 2:1 to 1:20, and more preferably 1:1 to 1:10. A carrier gas may also be used in the epoxidation process. As the carrier gas, any desired inert gas can be used. The molar ratio of olefin to carrier gas is then preferably in the range of 100:1 to 1:10 and especially 20:1 to 1:10.

As the carrier gas, noble gases such as helium, neon, and argon are suitable in addition to nitrogen and carbon dioxide. Saturated hydrocarbons with 1-8, especially 1-6, and preferably with 1-4 carbon atoms, e.g., methane, ethane, propane, and n-butane, are also suitable. Nitrogen and saturated $C_1$-$C_4$ hydrocarbons are the preferred inert carrier gases. Mixtures of the listed carrier gases can also be used.

Specifically in the epoxidation of propylene, propane or methane can be supplied in such a way that, in the presence of an appropriate excess of carrier gas, the explosive limits of mixtures of propylene, propane (methane), hydrogen, and oxygen are safely avoided and thus no explosive mixture can form in the reactor or in the feed and discharge lines.

Depending on the olefin to be reacted, the epoxidation according to the invention can be carried out in the liquid phase, the gas phase, or in the supercritical phase. When a liquid reaction medium is used, the catalyst mixture is preferably in the form of a suspension or fixed-bed. The process may be performed using a continuous flow, semi-batch or batch mode of operation.

If epoxidation is carried out in the liquid (or supercritical or subcritical) phase, it is advantageous to work at a pressure of 1-100 bars and in the presence of one or more solvents. Suitable solvents include any chemical that is a liquid under reaction conditions, including, but not limited to, oxygenated hydrocarbons such as alcohols, ethers, esters, and ketones, aromatic and aliphatic hydrocarbons such as toluene and hexane, nitrites such as acetonitrile, liquid $CO_2$ (in the supercritical or subcritical state), and water. Preferable solvents include liquid $CO_2$, nitrites, alcohols, ketones, and mixtures thereof, and mixtures of these solvents with water. Preferred nitrites include acetontrile and other nitriles with appreciable water solubility. Preferred alcohols include lower aliphatic $C_1$-$C_4$ alcohols such as methanol, ethanol, isopropanol, and tert-butanol, or mixtures thereof. Fluorinated alcohols can be used. It is particularly preferable to use mixtures of the cited alcohols with water.

If epoxidation is carried out in the liquid (or supercritical or subcritical) phase, it is advantageous to use a buffer. The buffer will typically be added to the solvent to form a buffer solution. The buffer solution is employed in the reaction to inhibit the formation of glycols or glycol ethers during epoxidation. Buffers are well known in the art.

Buffers useful in this invention include any suitable salts of oxyacids, the nature and proportions of which in the mixture, are such that the pH of their solutions may range from 3 to 10, preferably from 4 to 9 and more preferably from 5 to 7. Suitable salts of oxyacids contain an anion and cation. The anion portion of the salt may include anions such as phosphate, monohydrogenphosphate, dihydrogenphosphate, sulfate, carbonate, bicarbonate, carboxylates (e.g., acetate, phthalate, and the like), citrate, borate, hydroxide, silicate, aluminosilicate, or the like. The cation portion of the salt may include cations such as ammonium, alkylammoniums (e.g., tetraalkylammoniums, pyridiniums, and the like), alkali metals, alkaline earth metals, or the like. Examples include $NH_4$, $NBu_4$, $NMe_4$, Li, Na, K, Cs, Mg, and Ca cations. More preferred buffers include alkali metal phosphate and ammonium phosphate buffers. Buffers may preferably contain a combination of more than one suitable salt. Typically, the concentration of buffer in the solvent is from about 0.0001 M to about 1 M, preferably from about 0.001 M to about 0.3 M. The buffer useful in this invention may also include the addition of ammonia gas to the reaction system.

The following examples merely illustrate the invention. Those skilled in the art will recognize many variations that are within the spirit of the invention and scope of the claims.

EXAMPLE 1

Preparation of Pd—Pb/$TiO_2$ Catalysts

Catalyst 1A: Nitric Acid Added with Pd and Pb to $TiO_2$

Lead nitrate (0.35 g) is added to a nitric acid solution (5 mL of a 2.56 M $HNO_3$ (16.6% $HNO_3$ by volume), further diluted with 10 g distilled water; total acid solution=15 g). To this solution, an aqueous solution of palladium dinitrate (1.07 g, 20.64 wt. % Pd) is added with mixing. The Pd—Pb nitric acid solution is then added by incipient wetness to spray dried titania (20 g, 30 micron size, 40 $m^2$/g, calcined in air at 700° C.). The solids are calcined in air in a muffle furnace by heating at 110° C. for 4 hours (after ramping at 10° C./min) and then at 300° C. for 4 hours (after ramping at 2° C./min). The solids are calcined again in a muffle furnace by heating at 110° C; for 4 hours (after ramping at 10° C./min) and then heating at 600° C. for 4 hours (after ramping at 2° C./min). The solids are then transferred to a quartz tube and reduced with a 4 vol. % hydrogen in nitrogen stream at 100° C. for 1 hour (100 cc/hr), followed by nitrogen for 30 minutes while cooling from 100° C. to 30° C. to produce Catalyst 1A. Catalyst 1A contains 0.93 wt. % Pd, 0.9 wt. % Pb, and 57 wt. % Ti.

Catalyst 1B: Nitric Acid Added to $TiO_2$ before Pd and Pb Addition

An aqueous nitric acid solution (60 mL of a 2.56 M $HNO_3$ aqueous solution, 16.6% $HNO_3$ by volume) is added to spray dried titania (75 g, 30 micron size, 40 $m^2$/g, calcined in air at 700° C.) by incipient wetness. The nitric acid treated titania is calcined in a muffle furnace by heating at 110° C. for 4 hours (after ramping at 10° C./min) and then at 300° C. for 4 hours (after ramping at 2° C./min). Lead nitrate (0.17 g) is added to deionized water (8 g) to form a lead nitrate solution, and an aqueous solution of palladium dinitrate (0.53 g, 20.64 wt. % Pd) is added to the lead nitrate solution with mixing. The Pd—Pb solution is then added by incipient wetness to the nitric acid treated spray dried titania (10 g). The solids are then calcined and reduced according to the procedure of Catalyst 1A to produce Catalyst 1B. Catalyst 1B contains 0.95 wt. % Pd, 0.9 wt. % Pb, and 57 wt. % Ti.

Comparative Catalyst 1C: No Nitric Acid

Lead nitrate (0.35 g) is added to 14.5 mL of deionized water (14.5 mL) to form a lead nitrate solution, and an aqueous solution of palladium dinitrate (1.07 g, 20.64 wt. % Pd) is added with mixing. The Pd—Pb solution is then added by incipient wetness to spray dried titania (20 g, 30 micron size, 40 $m^2$/g, calcined in air at 700° C.). The solids are then calcined and reduced according to the procedure of Catalyst 1A to produce Comparative Catalyst 1C. Comparative Catalyst 1C contains 0.9 wt. % Pd, 0.9 wt. % Pb, and 58 wt. % Ti.

EXAMPLE 2

Preparation of Pd/$TiO_2$ Catalysts

Comparative Catalyst 2: Nitric Acid Added with Pd to $TiO_2$

An aqueous solution of palladium dinitrate (2.13 g, 20.64 wt. % Pd) is added to an aqueous solution of nitric acid (10 mL of a 2.5 M $HNO_3$ further diluted with 19 mL of distilled water) with mixing. The Pd, nitric acid solution is then added by incipient wetness to spray dried titania (40 g, 30 micron size, 40 $m^2$/g, calcined in air at 700° C.). The solids are then calcined and reduced according to the procedure of Catalyst 1A to produce Comparative Catalyst 2. Comparative Catalyst 2 contains 0.9 wt. % Pd and 57 wt. % Ti.

EXAMPLE 3

Epoxidation Reactions

A 300 cc stainless steel reactor is charged with the supported noble metal catalyst (0.07 g of 1A, 1B, 1C, or 2), TS-1 powder (0.63 g), methanol (~100 g), and a buffer solution (13 g of 0.1 M aqueous ammonium phosphate, pH=6). The reactor is then charged to 300 psig with a feed consisting of 4% hydrogen, 4% oxygen, 5% propylene, 0.5% methane and the balance nitrogen (volume %). The pressure in the reactor is maintained at 300 psig via a backpressure regulator with the feed gases passed continuously through the reactor at 1600 cc/min (measured at 23° C. and one atmosphere pressure). In order to maintain a constant solvent level in the reactor during the run, the oxygen, nitrogen and propylene feeds are passed through a two-liter stainless steel vessel (saturator) preceding the reactor, containing 1.5 liters of methanol. The reactor is stirred at 1500 rpm. The reaction mixture is heated to 60° C. and the gaseous effluent is analyzed by an online GC every hour and the liquid analyzed by offline GC at the end of the 18 hour run. Propylene oxide and equivalents ("POE"), which include propylene oxide ("PO"), propylene glycol ("PG"), and propylene glycol methyl ethers (PMs), are produced during the reaction, in addition to propane formed by the hydrogenation of propylene.

The epoxidation results (see Table 1) show that a TS-1 and Pd—Pb/TiO2 mixed catalyst shows a significantly reduced propane make (i.e., higher propylene selectivity) when the $TiO_2$ has been treated with $HNO_3$, compared to mixtures of TS-1 with Pd—Pb/$TiO_2$ that were not treated with $HNO_3$. In addition, $HNO_3$ treated Pd/$TiO_2$ (with no lead) produces an extremely high amount of propane.

TABLE 1

Epoxidation Results

| Catalyst | Catalyst Productivity[1] | Propane Make (%)[2] |
|---|---|---|
| 1A | 0.65 | 6 |
| 1B | 0.59 | 4 |
| 1C* | 0.7 | 12 |
| 2* | 0.7 | 26 |

[1]Productivity = grams POE produced/gram of catalyst per hour.
[2]Propane Make = moles propane/(moles POE + moles propane) × 100.
*Comparative Example

I claim:

1. A process for producing an epoxide comprising reacting an olefin, hydrogen and oxygen in the presence of a titanium or vanadium zeolite and a supported catalyst comprising palladium, lead and a carrier that has been treated by contacting with nitric acid.

2. The process of claim 1 wherein the titanium or vanadium zeolite is a titanium silicalite.

3. The process of claim 1 wherein the olefin is a $C_2$-$C_6$ olefin.

4. The process of claim 1 wherein the reaction is performed in the presence of a solvent selected from the group consisting of alcohols, ketones, nitriles, water, liquid $CO_2$, and mixtures thereof.

5. The process of claim 1 wherein the carrier is selected from the group consisting of titania, zirconia, niobia, silica, tantalum oxide, titania-silica, zirconia-silica, niobia-silica, and mixtures thereof.

6. A supported catalyst comprising palladium, lead, and a carrier that has been treated by contacting with nitric acid.

7. The supported catalyst of claim 6 wherein the carrier is selected from the group consisting of titania, zirconia, niobia, silica, tantalum oxide, titania-silica, zirconia-silica, niobia-silica, and mixtures thereof.

8. The supported catalyst of claim 7 wherein the carrier is titania.

9. The supported catalyst of claim 8 wherein the titania is contacted with nitric acid prior to introduction of the noble metal and the lead.

10. A catalyst mixture comprising a titanium or vanadium zeolite and a supported catalyst comprising palladium, lead, and a carrier that has been treated by contacting with nitric acid.

11. The catalyst mixture of claim 10 wherein the titanium zeolite is a titanium silicalite.

12. The catalyst mixture of claim 11 wherein the titanium silicalite is TS-1 or Ti-MWW.

13. The catalyst mixture of claim 10 wherein the carrier is selected from the group consisting of titania, zirconia, niobia, silica, tantalum oxide, titania-silica, zirconia-silica, niobia-silica, and mixtures thereof.

* * * * *